United States Patent
Chalekian

(10) Patent No.: US 8,414,611 B2
(45) Date of Patent: Apr. 9, 2013

(54) MAIN VESSEL CONSTRAINING SIDE-BRANCH ACCESS BALLOON

(75) Inventor: Aaron Chalekian, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1391 days.

(21) Appl. No.: 11/592,365

(22) Filed: Nov. 3, 2006

(65) Prior Publication Data

US 2008/0109056 A1    May 8, 2008

(51) Int. Cl.
*A61M 29/00*    (2006.01)

(52) U.S. Cl. ............................................. 606/192

(58) Field of Classification Search .............. 623/1.11, 623/1.35; 606/191, 192, 194, 195, 198; 604/96.01, 604/97.01, 101.01, 101.02, 101.05, 103.07, 604/103.08, 103.11, 916
See application file for complete search history.

(56) References Cited

U.S. PATENT DOCUMENTS

| | | | |
|---|---|---|---|
| 388,510 A * | 8/1888 | Terrell | 604/41 |
| 550,238 A | 11/1895 | Allen, Jr. | |
| 4,338,942 A | 7/1982 | Fogarty | |
| 4,490,421 A | 12/1984 | Levy | 428/35 |
| 4,546,759 A | 10/1985 | Solar | |
| 4,581,017 A | 4/1986 | Sahota | |
| 4,744,366 A | 5/1988 | Jang | |
| 4,763,654 A | 8/1988 | Jang | |
| 4,906,244 A | 3/1990 | Pinchuk et al. | 606/194 |
| 4,950,239 A | 8/1990 | Gahara et al. | 604/96 |
| 4,958,634 A | 9/1990 | Jang | |
| 4,994,033 A | 2/1991 | Shockey et al. | |
| 5,002,532 A | 3/1991 | Gaiser et al. | |
| 5,019,042 A | 5/1991 | Sahota | |
| 5,250,069 A | 10/1993 | Nobuyoshi et al. | 606/192 |
| 5,264,260 A | 11/1993 | Saab | 428/35.5 |
| 5,270,086 A | 12/1993 | Hamlin | 428/35.2 |
| 5,273,536 A | 12/1993 | Savas | |
| 5,304,135 A | 4/1994 | Shonk | |
| 5,308,323 A | 5/1994 | Sogawa et al. | |
| 5,328,468 A | 7/1994 | Kaneko et al. | 604/96 |
| 5,344,400 A | 9/1994 | Kaneko et al. | 604/96 |
| 5,415,635 A | 5/1995 | Bagaoisan et al. | |
| 5,500,180 A | 3/1996 | Anderson et al. | 264/532 |
| 5,536,252 A | 7/1996 | Imran et al. | |
| 5,556,383 A | 9/1996 | Wang et al. | 604/96 |

(Continued)

FOREIGN PATENT DOCUMENTS

| | | |
|---|---|---|
| EP | 1512381 | 9/2005 |
| WO | WO 97/17101 | 5/1997 |

(Continued)

OTHER PUBLICATIONS

International Search Report for PCT/US07/19837, which claims priority to the present application.

(Continued)

*Primary Examiner* — Ryan Severson
*Assistant Examiner* — David Eastwood

(57) ABSTRACT

A catheter having a multi-chamber balloon which includes a first chamber having a globular configuration and an adjacent second chamber having a generally cylindrical body portion are sequentially inflatable so when employed to enlarge an opening through a stent deployed at a bifurcation the stent is supported around the circumference of the side-branch opening while the stent wall opening is being enlarged.

15 Claims, 7 Drawing Sheets

U.S. PATENT DOCUMENTS

| | | | |
|---|---|---|---|
| 5,632,762 A * | 5/1997 | Myler | 606/194 |
| 5,749,890 A * | 5/1998 | Shaknovich | 606/198 |
| 5,797,877 A | 8/1998 | Hamilton et al. | 604/96 |
| 5,833,657 A | 11/1998 | Reinhardt et al. | 604/96 |
| 5,865,801 A | 2/1999 | Houser | |
| 5,868,777 A * | 2/1999 | Lam | 606/194 |
| 5,922,021 A | 7/1999 | Jang | 623/1 |
| 6,022,359 A | 2/2000 | Frantzen | |
| 6,086,548 A | 7/2000 | Chaisson et al. | |
| 6,123,721 A | 9/2000 | Jang | 623/1 |
| 6,146,356 A | 11/2000 | Wang et al. | 604/96 |
| 6,210,429 B1 | 4/2001 | Vardi et al. | 623/1.11 |
| 6,235,053 B1 | 5/2001 | Jang | 623/1.15 |
| 6,261,319 B1 | 7/2001 | Kveen et al. | 623/1.15 |
| 6,270,522 B1 | 8/2001 | Simhambhatla et al. | 623/1.11 |
| 6,334,870 B1 | 1/2002 | Ehr et al. | 623/1.16 |
| 6,348,065 B1 | 2/2002 | Brown et al. | 623/1.16 |
| 6,471,720 B1 | 10/2002 | Ehr et al. | 623/1.15 |
| 6,478,816 B1 | 11/2002 | Kveen et al. | 623/1.15 |
| 6,488,653 B1 | 12/2002 | Lombardo | |
| 6,524,302 B2 | 2/2003 | Kelley | |
| 6,527,739 B1 | 3/2003 | Bigus et al. | |
| 6,582,396 B1 | 6/2003 | Parodi | |
| 6,746,479 B2 | 6/2004 | Ehr et al. | 623/1.16 |
| 6,776,771 B2 | 8/2004 | van Moorlegem et al. | |
| 6,818,014 B2 | 11/2004 | Brown et al. | 623/1.16 |
| 6,835,203 B1 | 12/2004 | Vardi et al. | 623/1.34 |
| 6,905,490 B2 | 6/2005 | Parodi | |
| 6,966,889 B2 | 11/2005 | Saab | |
| 2002/0116047 A1 | 8/2002 | Vardi et al. | |
| 2002/0165521 A1 * | 11/2002 | Cioanta et al. | 604/509 |
| 2002/0173840 A1 | 11/2002 | Brucker et al. | 623/1.16 |
| 2002/0193873 A1 | 12/2002 | Brucker et al. | 623/1.35 |
| 2003/0097169 A1 | 5/2003 | Brucker et al. | 623/1.11 |
| 2003/0109909 A1 | 6/2003 | Ledesma et al. | |
| 2003/0195606 A1 | 10/2003 | Davidson et al. | 623/1.11 |
| 2004/0054362 A1 * | 3/2004 | Lopath et al. | 606/27 |
| 2004/0088007 A1 | 5/2004 | Eidenschink | 607/1 |
| 2004/0138732 A1 | 7/2004 | Suhr et al. | 623/1.11 |
| 2004/0147811 A1 | 7/2004 | Diederich et al. | |
| 2004/0172121 A1 | 9/2004 | Eidenschink et al. | 623/1.11 |
| 2005/0015108 A1 | 1/2005 | Williams et al. | 606/194 |
| 2005/0075662 A1 * | 4/2005 | Pedersen et al. | 606/194 |
| 2005/0119731 A1 | 6/2005 | Brucker et al. | 623/1.35 |
| 2005/0149161 A1 | 7/2005 | Eidenschink et al. | 623/1.11 |
| 2005/0154442 A1 | 7/2005 | Eidenschink et al. | 623/1.11 |
| 2005/0177221 A1 | 8/2005 | Mustapha | 623/1.11 |
| 2005/0192656 A1 | 9/2005 | Eidenschink | 623/1.11 |
| 2005/0234499 A1 | 10/2005 | Olson et al. | |
| 2005/0261722 A1 * | 11/2005 | Crocker et al. | 606/192 |
| 2006/0064064 A1 | 3/2006 | Jang | 604/194 |
| 2006/0116748 A1 | 6/2006 | Kaplan et al. | 623/1.11 |
| 2006/0265041 A1 * | 11/2006 | Sanati et al. | 623/1.11 |
| 2006/0287712 A1 | 12/2006 | Eidenschink | 623/1.35 |
| 2007/0038283 A1 | 2/2007 | Mustapha | |
| 2007/0050016 A1 | 3/2007 | Gregorich et al. | |
| 2007/0067011 A1 * | 3/2007 | Krolik et al. | 623/1.11 |
| 2007/0208411 A1 | 9/2007 | Meyer et al. | |
| 2008/0109062 A1 | 5/2008 | Chalekian | |

FOREIGN PATENT DOCUMENTS

| | | |
|---|---|---|
| WO | WO 99/36015 | 7/1999 |
| WO | WO 2005/041810 | 5/2005 |
| WO | 2005/084745 | 9/2005 |
| WO | 2006/085304 | 8/2006 |

OTHER PUBLICATIONS

U.S. Appl. No. 11/592,691, filed Nov. 3, 2006, Chalekian.
International Search Report for PCT/US07/19836, which claims priority to U.S. Appl. No. 11/592,691.

* cited by examiner

MAIN VESSEL CONSTRAINING SIDE-BRANCH ACCESS BALLOON

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents and other radially expandable endoprostheses are typically implanted transluminally and enlarged radially after being introduced percutaneously. Such endoprostheses may be implanted in a variety of body lumens or vessels such as within the vascular system, urinary tracts, bile ducts, fallopian tubes, coronary vessels, secondary vessels, etc. Some may be used to reinforce body vessels and/or to prevent restenosis following angioplasty in the vascular system. They may be self-expanding, expanded by an internal radial force, such as when mounted on a balloon, or a combination of self-expanding and balloon expandable (hybrid expandable).

Within the vasculature it is not uncommon for stenoses to form at a vessel bifurcation. A bifurcation is an area of the vasculature or other portion of the body where a first component vessel divides into two or more component vessels. Where a stenotic lesion or lesions form at such a bifurcation, the lesion(s) can affect one, two or all three of the involved vessels.

Many of the stents that have been disclosed for deployment at bifurcations are deployed as a first stent, extending from one component vessel into a second, crossing the vessel opening ("ostium) into the third vesssel. After the stent has been deployed, an opening in the stent side-wall disposed at the ostium can then be enlarged by placing a balloon therethrough and expanding the balloon. This opening enlargement facilitates fluid flow into or from the third vessel. If needed, a second stent may also be placed in the third vessel. For a variation of this procedure, many stent configurations have been designed which have a specialized side-branch opening through which the opening into the third vessel may be provided. Often such designs include a portion of the first stent which is displaced into and against the side-wall of the third vessel for a short distance beyond the ostium.

In such stent placement procedures the balloon used to provide enlargement of the side-wall opening may be a conventional cylindrical balloon, or a stepped balloon having two cylindrical portions the distal portion typically having a smaller diameter than the proximal portion. However, use of these balloons has not always been fully satisfactory. For instance, in some applications the side-wall opening enlargement has been observed to cause an inward displacement of a portion of the stent into the second vessel flow channel, thereby potentially facilitating restenosis or otherwise disrupting the flow in the second vessel.

BRIEF SUMMARY OF THE INVENTION

The present invention is directed to a balloon configuration developed particularly for performing a side-wall opening enlargement procedure which has a substantially reduced likelihood of producing such inward displacement. In some embodiments the invention pertains to a multi-chamber balloon which includes a first chamber having a globular configuration and an adjacent second chamber having a generally cylindrical body portion. When mounted on a catheter the chambers are sequentially inflatable so when employed to enlarge an opening through a stent deployed at a bifurcation the stent is supported around the circumference of the side-branch opening while the stent wall opening is being enlarged.

In one aspect the invention pertains to a medical device balloon, the balloon having a longitudinal axis and comprising:

a first chamber having a globular configuration with a maximum perpendicular dimension (D1) taken in a plane perpendicular to the longitudinal axis of the balloon and an axial length (D3) which is not more than about 20% greater than the maximum perpendicular dimension (D1), and an adjacent second chamber having a generally cylindrical body portion which has a diameter (D2) which is less than the first chamber diameter axial length (D3).

In another aspect the invention pertains to a catheter having such balloons mounted thereon. Such catheters being particularly suited to enlarging a side-wall opening in a stent that has been placed at a bifurcation.

In still further aspect the invention pertains to a method for deploying a stent having at least one side-wall opening at a bifurcation comprising first, second and third vessels, a channel between the first and second vessels and an ostium into the third vessel, the method comprising:

deploying the stent in said channel between the first and second vessels to engage the vessel walls thereof and cross the ostium with a side-wall opening facing the ostium and enlarging said stent side-wall opening facing the ostium by passing a balloon catheter through the stent side-wall opening and into the third vessel such that the catheter balloon crosses the stent side-wall opening and then expanding the balloon, wherein the balloon catheter employed to enlarge the stent opening has a balloon as described herein mounted thereon.

These and other aspects of the invention are described further in the description, figures and claims which follow.

BRIEF DESCRIPTION OF THE SEVERAL VIEWS OF THE DRAWING(S)

DETAILED DESCRIPTION OF THE INVENTION

Figure 1:
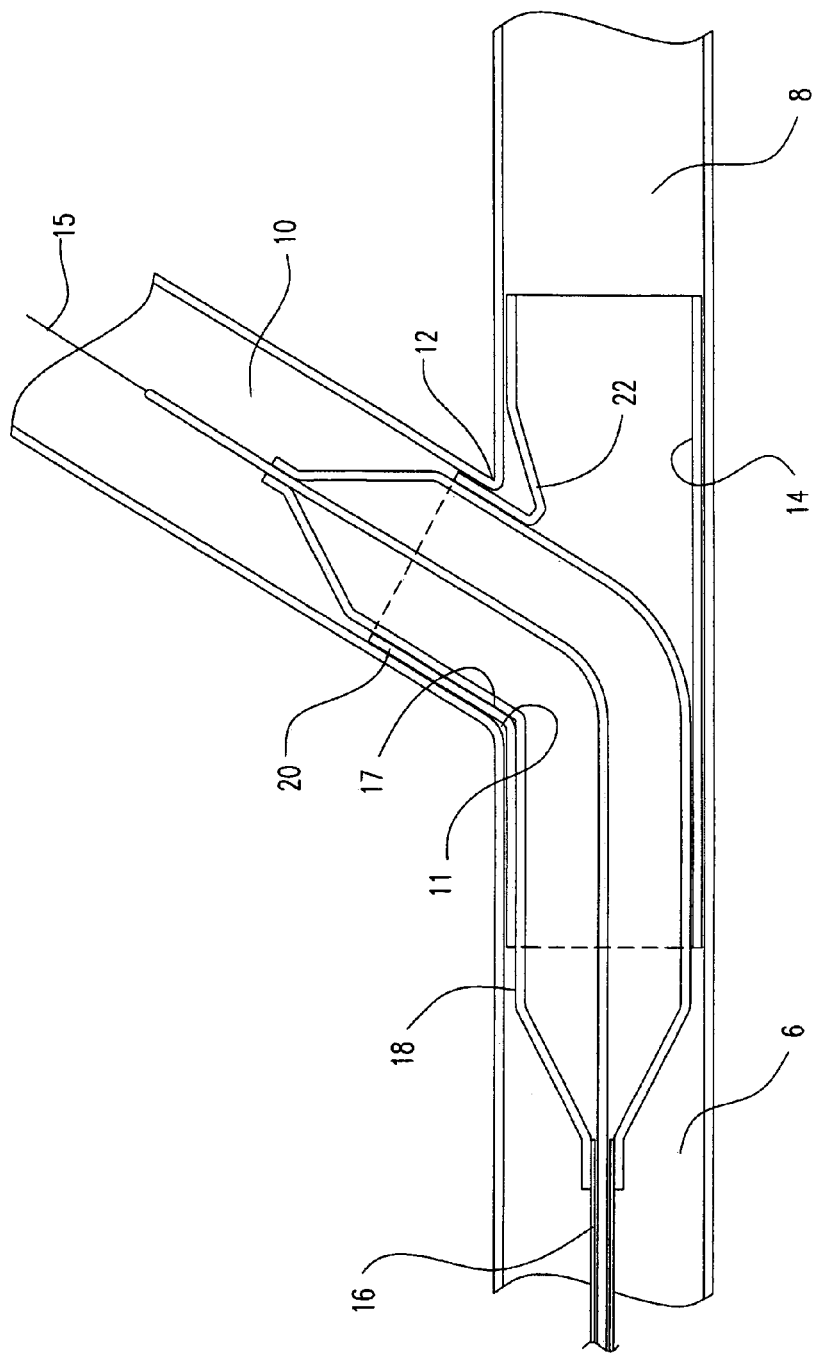
FIG. 1 is a longitudinal side sectional view of a vessel bifurcation illustrating a prior art process for enlarging a stent side-wall opening.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall be taken as referring to like features unless otherwise indicated. All US patents and applications and all other published documents mentioned anywhere in this application are incorporated herein by reference in their entirety.

Referring first to a depiction of prior art, a bifurcated blood vessel is shown in FIG. 1. Components of the bifurcation are first vessel 6, second vessel 8 and third vessel 10. In this particular embodiment the first and second vessels taken together form a main channel with the third vessel forming a branch vessel having an opening 11 to the main channel, but there is no particular requirement that the bifurcation form distinct main and side channels. At one side of the opening 11 (the ostium), between the vessels 8 and 10, is a carina region 12. A stent 14 is deployed at the bifurcation, extending from the first vessel into second vessel and crossing the ostium. In accordance with a prior art procedure as previously described a guide wire 15 has been passed through the first vessel into the third vessel passing through the side-wall opening 17 of the stent 14 and a catheter 16 provided thereover. The catheter 16 has a balloon 18 that crosses between the first and second vessels and has been inflated to expand the side-wall opening 17. In this particular depiction a portion 20 of the stent sidewall is configured to extend into the third vessel channel when the balloon 18 is inflated in the side-wall opening, but such a configuration is not a necessary feature of stents employed in the process.

FIG. 1 shows that the expansion of the balloon 18 through the stent side-wall has caused an inward displacement of a portion 22 of the stent away from the carina 12. The stent portion 22 has moved into the flow channel of the second vessel, thereby potentially facilitating restenosis or otherwise disrupting the flow in the second vessel.

Figure 2:
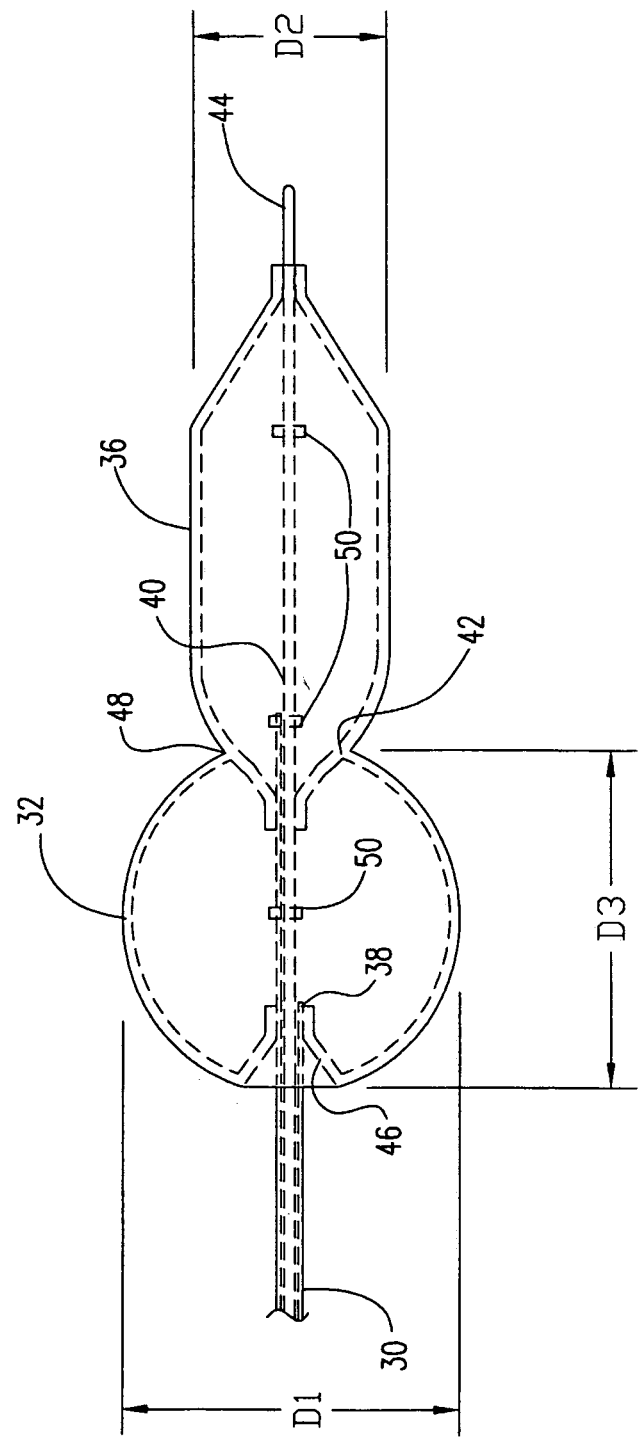
FIG. 2 is a side view of a catheter distal portion on which is mounted a balloon according to one embodiment of the invention.

FIG. 2 shows a configuration for a catheter 30 of the invention having a balloon 32 of the present invention mounted thereon. Balloon 32 includes two adjacent portions 34, 36 that are separately inflatable. Separate lumens 38, 40 are provided in catheter 30 for inflation of the respective balloon portions 34, 36. A common wall 42 is provided at the junction between portions 34 and 36.

Portion 34 of the balloon 34 has a globular shape, for instance it may be spherical or generally spherical. Balloon portion 36 has a generally cylindrical configuration. The portions are sized relative to each other such that a maximum perpendicular dimension D1 taken in a plane perpendicular to the axis of the balloon, is larger than the dimension D2, corresponding to the diameter of the cylindrical portion 36 and larger than the major dimension of the ostium of the branch opening across which the stent is to be placed. D3, the longitudinal length of the globular portion, may be somewhat less than D1 due to truncation at one or both ends of the globular portion 34 along the balloon axis, but is suitably at least slightly larger than the diameter of the first stent after vessel placement and also larger than the diameter D2 of the cylindrical portion 36.

Truncation of the axial length of portion 34 occurs at least at the junction with portion 36. The balloon portion 34 at its proximal end is preferably, but not necessarily, mounted on the catheter in everted fashion to facilitate the angular bending of the catheter into the side branch. In at least some embodiments an inverted conical portion 46 is provided to further assist the catheter bending into the side branch truncating the axial length of portion 34 somewhat at the proximal end as well.

At the junction between balloon portions a neck region 48 occurs where the balloon transitions between portion 36 to 34. In at least some embodiments the inflated balloon diameter at neck 48 is less than D2.

Catheter 30 has an inner shaft 44 that extends through both balloon portions to provide a guide wire lumen. Radiopaque markers 50 may be provided to facilitate fluoroscopic location of the catheter in processing. In some embodiments such markers may be provided along the inner shaft within the globular portion 34 of the balloon 36, for instance near the longitudinal center thereof, and within the cylindrical portion, for instance near the ends of the cylindrical portion. Other locations may be marked in addition or in alternative to these locations.

Figure 3:
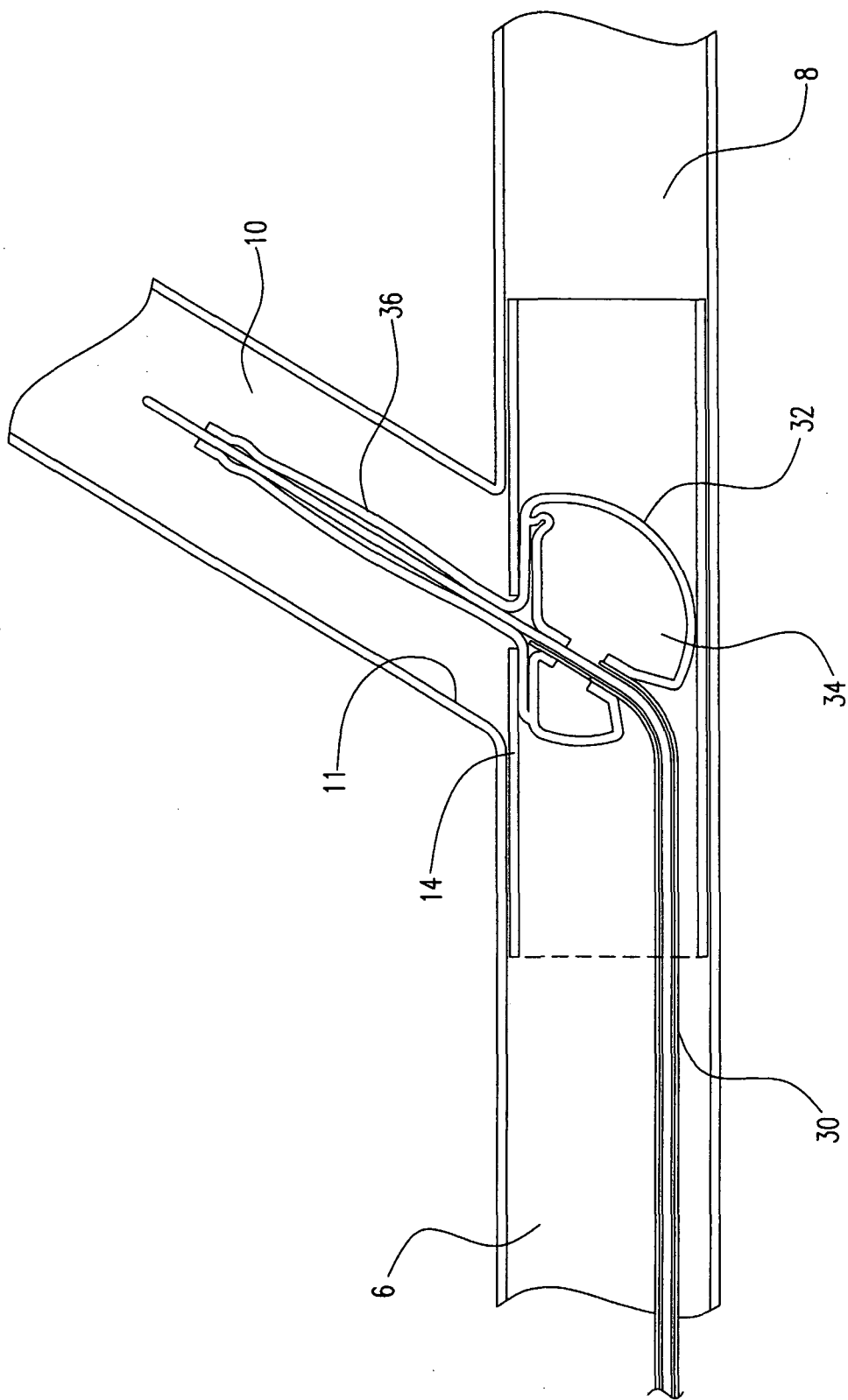
FIG. 3 is a longitudinal side sectional view of a vessel bifurcation illustrating an inventive process for enlarging a stent side-wall opening using the catheter of FIG. 2, with the balloon partially inflated.

FIG. 3 is a view similar to that of FIG. 1, but with a catheter 30 of the invention extending through the stent side-wall into the side channel. Portion 34 of the balloon 32 has been partially inflated, but portion 36 remains uninflated and so the stent side-Wall opening has not been enlarged.

Figure 4:
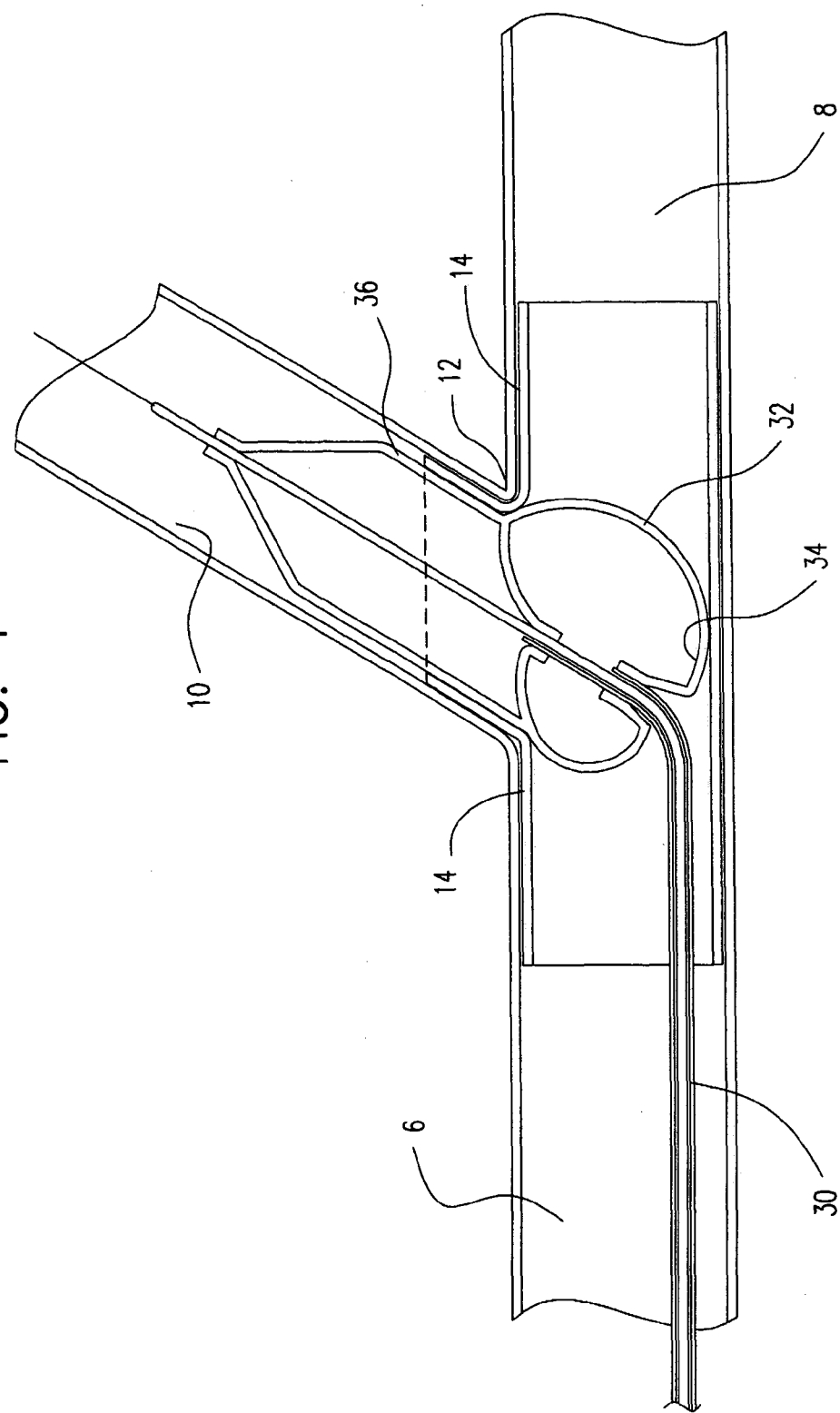
FIG. 4 is view as in FIG. 3 with the balloon fully inflated.

FIG. 4 is a view as in FIG. 3, but with both balloon portions fully inflated. The stent is engaged circumferentially around the ostium by the larger size of the balloon portion 34, including the stent portion in the vicinity of the carina 12. Thus the balloon supports the carina and minimizes or eliminates inward deflection of the stent 14 into the flow path of the second vessel, solving the problem of the prior art procedure.

Subsequent to the deployment of the catheter 30 to enlarge the stent opening the balloon sections are deflated and the catheter is removed. If desired a second stent may be placed in the third vessel 10.

Figure 5:
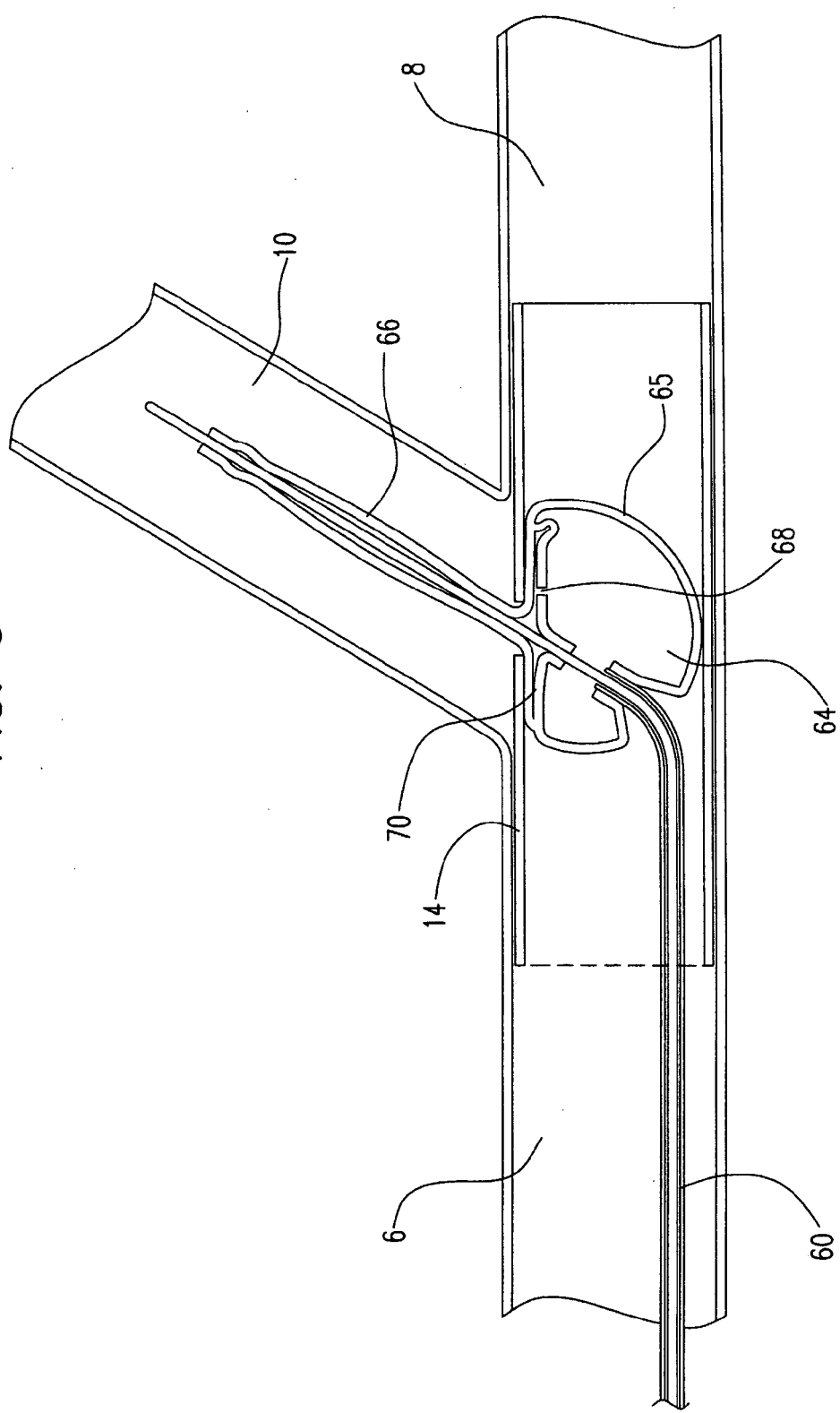
FIG. 5 is a view as in FIG. 3 employing a catheter having a balloon according to an alternate embodiment of the invention.
Figure 6:
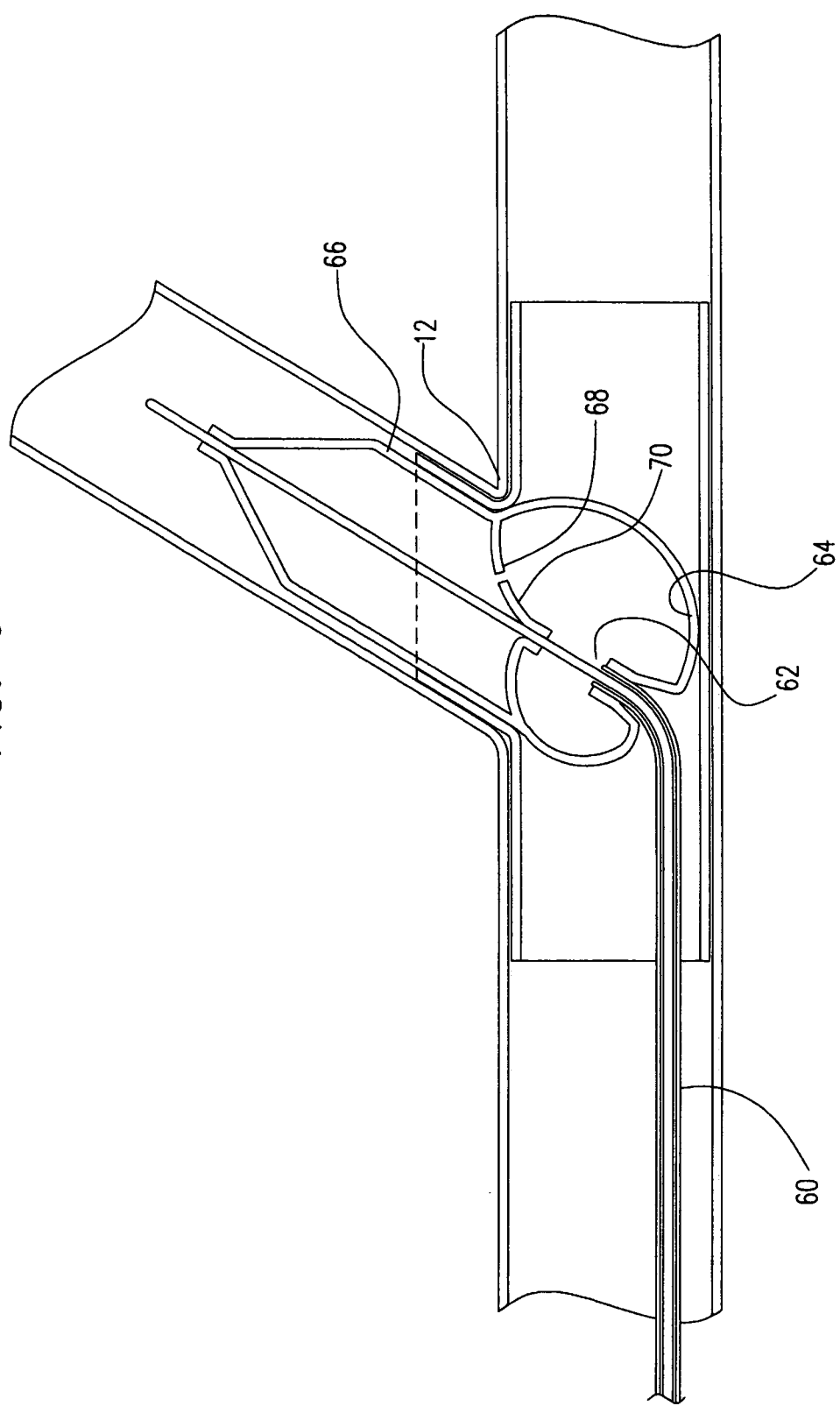
FIG. 6 is a view as in FIG. 5 with the balloon fully inflated.

FIGS. 5 and 6 are views as in FIGS. 3 and 4, respectively, depicting an alternate embodiment of the invention. The catheter 60 is provided with a single balloon inflation lumen 62 which opens into globular balloon portion 64 of the balloon 65. A separate lumen is not provided to the cylindrical portion 66 of the balloon 65. Instead a small opening 68 in the wall 70 between portions 64 and 66 is provided so that inflation of portion 66 is accomplished through the single lumen. Suitably the opening is sized so that inflation of portion 66 occurs at a delayed sequence relative to portion 64 as the balloon is pressurized. Such a delay sequence allows portion 64 to supportively engage the stent in the region of the carina 12 as the stent opening is enlarged in a manner similar to that of the balloon 32 of the previous embodiment. In some embodiments the opening 68 may be provided as a pressure responsive valve (not shown) which opens only when the pressure in portion 34 reaches a minimum pressure, for instance 4-10 atm.

Figure 7:
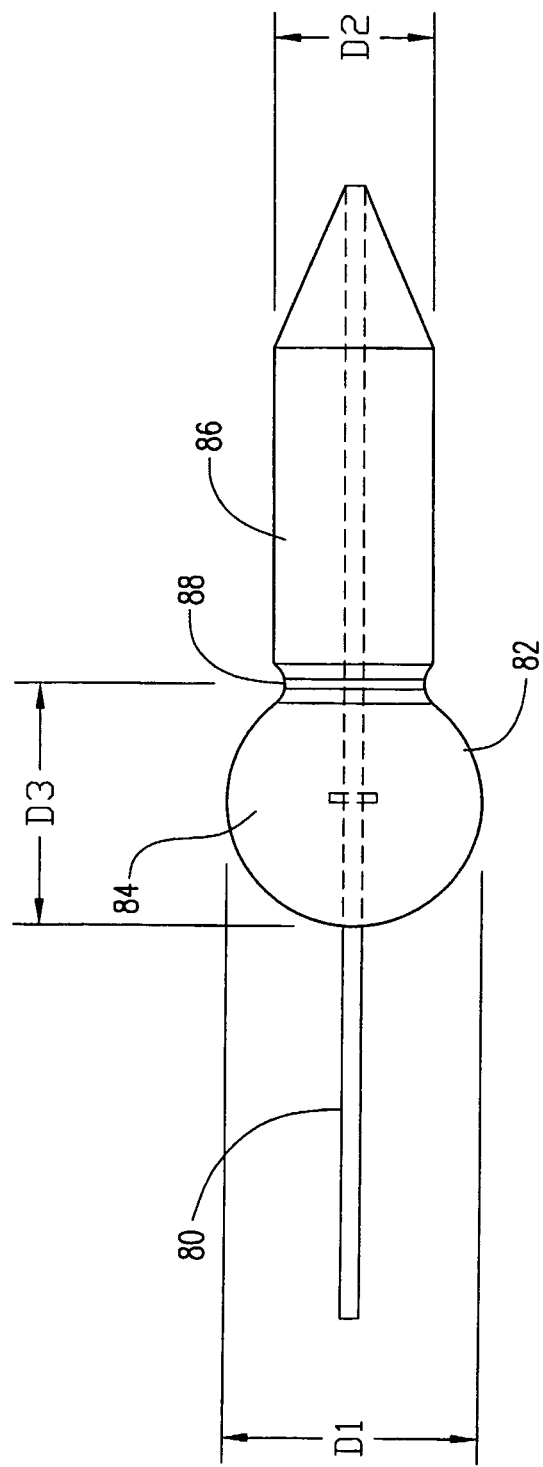
FIG. 7 is a view of a catheter distal portion as in FIG. 2 but with a further alternate embodiment of a balloon of the invention.

FIG. 7 is a view similar to FIG. 2 showing another variation of the invention balloon 82 mounted on the catheter 80. In FIG. 7, at the junction between the two balloon portions 84 and 86, the indented neck 88 is formed with a fixed diameter when the balloon is inflated that is less the diameter D2 of the cylindrical portion. The fixed diameter configuration of neck 88 may be formed by molding or the like.

The necks 48 and 88 in FIGS. 2 and 7, respectively, may facilitate a secure engagement of the stent in the carina region 12 by the globular portion 34 as the cylindrical portion inflates and enlarges the stent wall opening and/or facilitate self-centering of the globular portion around the circumference of the bifurcation ostium.

Referring again to FIGS. 2 and 7, exemplary dimensions are taken at a nominal inflation pressure, suitably about 2 to about 6 atm, for instance 4 atm. Without limitation, D2 may be from about 1 mm to about 20 mm. In some embodiments D1 may be for instance from 10-50% larger than D2. In some embodiments the shoulder 48 in FIG. 2 or formed neck 88 are indented for instance to a minimum diameter which is 2-20% less than D2.

In the embodiments shown in the figures the globular portions 34, 64 or 84 of the balloons of the invention are substantially spherical with truncations along the axial axis which render the axial length D3 less than the maximum perpendicular dimension D1. In other embodiments the overall shape of the balloon may be more ellipsoid or ovoid than spherical. In such embodiments, however, the axial length suitably will not more than about 20% greater than the maximum perpendicular dimension D1 and more suitably will be equal or less than the D1 dimension. Also suitably the D3 dimension will be larger than the diameter (D2) of the cylindrical portion of such balloons. Likewise, in use, a balloon size will be selected in which the axial length D3 of the globular portion is greater than the diameter of the stent as deployed.

The balloon may be made of known balloon polymer materials. Examples of known materials include polyesters, polyolefins, nylons, polyurethanes and various block copolymers. Exemplary documents describing suitable materials which may be employed in the invention include: U.S. Pat. No. 4,490,421 Levy, and U.S. Pat. No. 5,264,260, Saab, which describe PET balloons; U.S. Pat. No. 4,906,244, Pinchuk et al, and U.S. Pat. No. 5,328,468, Kaneko, which describe polyamide balloons; U.S. Pat. No. 4,950,239, Gahara, and U.S. Pat. No. 5,500,180, Anderson et al which describe balloons made from polyurethanes; U.S. Pat. No. 5,556,383, Wang et al, and U.S. Pat. No. 6,146,356, Wang et al, which describe balloons made from polyether-block-amide copolymers and polyester-block-ether copolymers; U.S. Pat. No. 6,270,522, Simhambhatla, et al, describes balloons made from polyester-block-ether copolymers; U.S. Pat. No. 5,344,400, Kaneko, which describes balloons made from polyarylene sulfide; U.S. Pat. No. 5,833,657, Reinhart et al, describes balloons having a layer of polyetheretherketone. All of these balloons are produced from extruded tubing of the polymeric material by a blow-forming radial expansion process. U.S. Pat. No. 5,250,069, Nobuyoshi et al, U.S. Pat. No. 5,797,877, Hamilton et al, and U.S. Pat. No. 5,270,086, Hamlin, describe still further materials which may be used to make such balloons. Physical blends and copolymers of such materials may also be used.

The balloon may be a laminate of two or more layers of the same or different polymers or blends of polymers as described above. Moreover the two balloon portions 34 and 36 may be made of the same or different polymers, blends or laminates.

In some embodiments, exemplary configurations of a stent body may be as described in the following patents: U.S. Pat. No. 6,746,479; U.S. Pat. No. 6,478,816; U.S. Pat. No. 6,471,720; U.S. Pat. No. 6,334,870; U.S. Pat. No. 6,261,319; U.S. Pat. No. 6,818,014; U.S. Pat. No. 6,348,065; U.S. Pat. No. 5,922,021; U.S. Pat. No. 6,235,053; U.S. Pat. No. 6,835,203; U.S. Pat. No. 6,210,429 and/or U.S. Pat. No. 6,123,721, the entire contents of each of which are incorporated herein by reference. US patent applications, also incorporated herein by reference in their entirety, that describe various stents for deployment at bifurcations or systems for deploying stents at bifurcations include:

U.S. application Ser. No. 11/155,155, filed Jun. 17, 2005, titled "Bifurcation Stent Assembly";
US 20040138736, titled "Bifurcated stent";
US 20050192656, titled "Bifurcated Stent Delivery System";
US 20050154442, titled "Bifurcated stent delivery system";
US 20050149161, titled "Edge protection and bifurcated stent delivery system";
US 20050119731, titled "Bifurcated stent and delivery system";
US 20040172121, titled "Rotating balloon expandable sheath bifurcation delivery";
US 20040138736, titled "Bifurcated stent";
US 20040088007, titled "Asymmetric bifurcated crown";
US 20030097169, titled "Bifurcated stent and delivery system";
US 20020193873, titled "Bifurcated stent and delivery system";
US 20020173840, titled "Bifurcated stent";
US 20030195606, titled "Bifurcation stent system and method";
US 20040138732, titled "Apparatus and method for stenting bifurcation lesions";
US 20050015108, titled "Catheter Balloon Systems and Methods"; and
US 20060064064, titled "Two-step/dual-diameter balloon angioplasty catheter for bifurcation and side-branch vascular anatomy."

Stents as depicted in the foregoing published applications may also be employed. Initial deployment of the stent into a vessel bifurcation may be achieved in a variety of ways as described in any of the foregoing patents or published applications or by other techniques known in the art.

The stent may be made from any suitable biocompatible materials including one or more polymers, one or more metals or combinations of polymer(s) and metal(s). Examples of suitable materials include biodegradable materials that are also biocompatible. Suitable biodegradable materials include polylactic acid, polyglycolic acid (PGA), collagen or other connective proteins or natural materials, polycaprolactone, hylauronic acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol. At least a portion of the stent may be provided with material or thickness that enhances the radiopacity of the stent.

One or both of the first and second stents employed in the invention may carry one or more therapeutic agents which may be drugs or other pharmaceutical products for release at the site of deployment. The therapeutic agent may be, for instance, an anti-thrombogenic agent, vascular cell growth promoter, growth factor inhibitors, antibiotics, DNA, RNA, proteins, polysaccharides, heparin, dexamethasone, Paclitaxel, Zotarolimus, Sirolimus (i.e. rapamycin), Everolimus, phosphorylcholine, 17beta-estradiol, curcumin, malononitrilamide (e.g. malononitrilamide FK778), statins (e.g. fluvastatin), eptifibatide, irinotecan, triclosan, integrin-binding cyclic Arg-Gly-Asp peptide, cytochalasin D, mitoxantrone, carvedilol, alpha-1-antitrypsin (AAT), methotrexate, methylprednisolone, controlled release nitrogen oxide donor, tumor necrosis factor-alpha antibody, ciprofloxacin, Argatroban, angiopeptin, etc. The therapeutic agent may be carried in a coating, for instance a polystyrene-polyisobutylene-polystyrene triblock copolymer (SIBS), polyethylene oxide, silicone rubber and/or any other suitable coating material or it may be embedded or otherwise entrained in the stent structure.

The stent may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the stent employed in the invention.

In another alternative embodiment the catheter upon which the balloon of the invention is mounted may be a fixed wire catheter or other type of catheter that is capable of being advanced through the vasculature or other body lumen(s).

In embodiments where the assembly comprises one or more therapeutic agents, an agent or agents present on the stent 30 may be similar or different to the agent or agents which may be present on the flap 40. The dosage of the agents on the stent and/or flap may vary or be different on different portions of the assembly.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A medical device balloon having a proximal end, a distal end, and a longitudinal axis, the balloon comprising: a first balloon portion at the proximal end of the balloon, the first balloon portion defining a first chamber and having a globular configuration with a maximum perpendicular dimension (D1) taken in a plane perpendicular to the longitudinal axis of the balloon and an axial length (D3) which is not more than about 20% greater than the maximum perpendicular dimension (D1), and an adjacent second balloon portion, the second balloon portion defining a second chamber and having a generally cylindrical body portion which has a diameter (D2) which is less than the first chamber diameter axial length (D3), wherein the first balloon portion is proximal of the second balloon portion, the first balloon portion has a proximal end that defines the proximal end of the balloon, the second balloon portion has a distal end that defines the distal end of the balloon, and the first balloon portion has an inwardly inverted conical portion disposed at the proximal end of the balloon.

2. A medical device balloon as in claim 1 wherein the globular configuration of the first chamber is generally spherical.

3. A medical device balloon as in claim 1 wherein the first and second chambers are separated by an imperforate wall.

4. A medical device balloon as in claim 1 wherein the first and second chambers are separated by a wall having one or more perforations or pressure openable valves.

5. A medical device balloon as in claim 1 having an exterior surface and a junction on the exterior surface where the two chambers meet.

6. A medical device balloon as in claim 5 wherein the junction is a circumferential neck which has a diameter less than the diameter (D2) of the second chamber.

7. A medical device balloon as in claim 5 wherein the junction is a neck portion having a minimum perpendicular dimension taken in a plane perpendicular to the longitudinal axis of the balloon that is less the diameter of the second balloon portion.

8. A catheter having a balloon as in claim 1 mounted on a distal portion thereof.

9. A catheter as in claim 8 further comprising separate inflation lumens for each of the first and second chambers.

10. A catheter as in claim 8 further comprising a guide wire lumen passing through the balloon.

11. A catheter as in claim 8 configured as a fixed wire catheter.

12. A catheter as in claim 8 having a single inflation lumen opening into the balloon first chamber and wherein the first and second chambers of the balloon are separated by a wall having one or more perforations or pressure openable valves therein.

13. A catheter as in claim 8 wherein the globular configuration of the first chamber is generally spherical.

14. A catheter as in claim 8 wherein the globular configuration of the first chamber is generally ellipsoid or ovoid.

15. A catheter having a proximal end and a distal end and a shaft with a balloon mounted on a distal portion thereof, the balloon having a proximal end, a distal end, and a longitudinal axis and comprising: a first chamber having a proximal end, a distal end, and a globular configuration with a maximum perpendicular dimension (D1) taken in a plane perpendicular to the longitudinal axis of the balloon and an axial length (D3) which is not more than about 20% greater than the maximum perpendicular dimension (D1), and an adjacent second chamber having a proximal end, a distal end, and a generally cylindrical body portion with a diameter (D2) which is less than the first chamber axial length (D3), wherein the first chamber is proximal of the second chamber, the first chamber has a proximal end that defines the proximal end of the balloon, the second chamber has a distal end that defines the distal end of the balloon, and the proximal end of the first chamber has an everted mounting to the catheter shaft.

* * * * *